United States Patent
Allen et al.

(10) Patent No.: US 9,695,385 B2
(45) Date of Patent: Jul. 4, 2017

(54) SURFACTANTS BASED ON MONOUNSATURATED FATTY ALCOHOL DERIVATIVES

(71) Applicant: Stepan Company, Northfield, IL (US)

(72) Inventors: David R Allen, Chicago, IL (US); Randal J Bernhardt, Antioch, IL (US); Aaron Brown, Chicago, IL (US); Gregory P Dado, Chicago, IL (US); Xue Min Dong, Lincolnshire, IL (US); Wilma Gorman, Park Ridge, IL (US); Ronald Masters, Glenview, IL (US); Patti Skelton, Winder, GA (US)

(73) Assignee: STEPAN COMPANY, Northfield, IL (US)

( * ) Notice: Subject to any disclaimer, the term of this patent is extended or adjusted under 35 U.S.C. 154(b) by 0 days.

(21) Appl. No.: 14/770,912

(22) PCT Filed: Mar. 5, 2014

(86) PCT No.: PCT/US2014/020890
§ 371 (c)(1),
(2) Date: Aug. 27, 2015

(87) PCT Pub. No.: WO2014/164156
PCT Pub. Date: Oct. 9, 2014

(65) Prior Publication Data
US 2016/0002571 A1  Jan. 7, 2016

Related U.S. Application Data

(60) Provisional application No. 61/780,604, filed on Mar. 13, 2013.

(51) Int. Cl.
*A01N 25/00* (2006.01)
*A01N 25/30* (2006.01)
*C07C 305/10* (2006.01)
*C11D 1/14* (2006.01)

(52) U.S. Cl.
CPC .............. *C11D 1/146* (2013.01); *A01N 25/00* (2013.01); *A01N 25/30* (2013.01); *C07C 305/10* (2013.01)

(58) Field of Classification Search
CPC .......... A61Q 19/00; A61Q 19/10; A61Q 5/02; A61Q 17/02; A61Q 17/04; A61Q 19/007; A61Q 5/00; A01N 25/30; A61K 2039/505; A61K 2039/507; A61K 35/18; A61K 38/168; A61K 8/463; A61K 9/1271
See application file for complete search history.

(56) References Cited

U.S. PATENT DOCUMENTS

| | | |
|---|---|---|
| 1,889,348 A | 11/1932 | Bruson et al. |
| 2,737,519 A | 3/1956 | Michailas et al. |
| 2,865,968 A | 12/1958 | Hansley et al. |
| 3,193,586 A | 7/1965 | Rittmeister |
| 3,544,613 A | 12/1970 | Knaggs et al. |
| 3,636,034 A | 1/1972 | Ohsumi et al. |
| 3,852,221 A * | 12/1974 | Bentley ................... C11D 1/655 510/429 |
| 3,875,202 A | 4/1975 | Steckler |
| 4,250,343 A | 2/1981 | Kaufhold et al. |
| 4,288,642 A | 9/1981 | Yamanaka et al. |
| 4,334,092 A | 6/1982 | Knifton |
| 4,447,659 A | 5/1984 | Blewett et al. |
| 4,545,941 A | 10/1985 | Rosenburg et al. |
| 4,642,364 A | 2/1987 | Chan et al. |
| 4,695,661 A | 9/1987 | Homann |
| 4,792,419 A | 12/1988 | Piorr et al. |
| 4,804,790 A | 2/1989 | Schuett et al. |
| 5,124,491 A | 6/1992 | Fleckenstein et al. |
| 5,446,188 A | 8/1995 | Gruber et al. |
| 5,672,781 A | 9/1997 | Koehler et al. |

(Continued)

FOREIGN PATENT DOCUMENTS

| | | | |
|---|---|---|---|
| ES | 2141678 | 3/2000 | |
| GB | 1018302 | 1/1966 | |
| GB | 2085881 | 5/1982 | |
| IE | 904601 | 6/1991 | |
| WO | 9113057 | 5/1991 | |
| WO | WO91/13057 | * 9/1991 | ........... C07C 305/10 |
| WO | 2013162736 A1 | 10/2013 | |

OTHER PUBLICATIONS

J. Sci. Ind. Res. B Physical (1954), 13B(4), 277-280.

(Continued)

*Primary Examiner* — Audrea Buckley
(74) *Attorney, Agent, or Firm* — Dilworth IP LLC

(57) ABSTRACT

Surfactant compositions comprising an alkoxylate, a sulfate, or ether sulfate of a $C_{10}$-$C_{12}$ monounsaturated alcohol are disclosed. The alkoxylate, sulfate, or ether sulfate may derive from undecylenic acid or undecylenic alcohol. Compared with their saturated analogs, the monounsaturated alkoxylates, sulfates, and ether sulfates are less irritating, making them valuable for personal care, laundry, cleaners, and other household applications. Microscopy studies show that the alkoxylates, sulfates, and ether sulfates have favorable phase behavior over a wide range of actives levels, expanding opportunities for products with greater compaction. When combined with cationic surfactants, the alkoxylates, sulfates, and ether sulfates exhibit synergy, and they have improved solubility compared with their saturated analogs. The surfactants find value for the personal care, laundry and cleaning, emulsion polymerization, agricultural products, oilfield applications, and specialty foams industries.

11 Claims, No Drawings

(56) References Cited

U.S. PATENT DOCUMENTS

| | | | |
|---|---|---|---|
| 5,981,812 A | 11/1999 | Eufinger et al. | |
| 6,342,208 B1* | 1/2002 | Hyldgaard | A61K 8/06 424/400 |
| 6,683,224 B1 | 1/2004 | Hourticolon et al. | |
| 6,723,867 B1 | 4/2004 | Huebner et al. | |
| 6,809,196 B2 | 10/2004 | Bamdad et al. | |
| 7,169,959 B2 | 1/2007 | Heck et al. | |
| 7,208,643 B2 | 4/2007 | Namba et al. | |
| 7,427,588 B2 | 9/2008 | Berger et al. | |
| 7,629,299 B2 | 12/2009 | Berger et al. | |
| 2010/0145086 A1 | 6/2010 | Schrodi et al. | |
| 2011/0113679 A1 | 5/2011 | Cohen et al. | |
| 2012/0035386 A1* | 2/2012 | Nguyen | A01N 25/30 558/34 |
| 2012/0071676 A1 | 3/2012 | Schrodi et al. | |

OTHER PUBLICATIONS

J.C.Mol, Green Chem. 4 (2002) 5.
X. Dominguez, J. Chem. Ed. 29 (1952) 446.
A. Gupta et al., J. Sci. Ind. Res. 13B (1954) 277 [abstract].
G. Das et al., J. Am. Oil Chem. Soc. 66 (1989) 938.
J. Sauer et al, J. Am. Chem. Soc. 59 (1937) 1.
C. Pale-Grosdemange et al., J. Am. Chem. Soc. 113 (1991) 12.
C. Akbay et al., Electrophoresis 25 (2004) 622 (abstract).
B. Boyer et al., New J. Chem. 16 (1992) 883 (abstract).
D. Glatzhofer et al., Langmuir 9 (1993) 2949.
H. Mutlu et al., Eur. J. Lipid Sci. Technol. 112 (2010) 10 (abstract).
A. Hubert et al., Synthesis (1969) 97 (Abstract).
H. Bestmann et al., Angew. Chem., Int. Ed. Engl. 4 (1965) 830 (abstract).
B. Schaub et al. Tetrahedron Lett. 26 (1985) 307 (abstract).
R. Monson et al., J. Org. Chem. 36 (1971) 3826.
T. Gibson et al., J. Org. Chem. 46 (1981) 1821.
G. Doyle, J. Catal. 30 (1973) 118 (abstract).
R. Spronk et al., Appl. Catal. 70 (1991) 295 (abstract).
H. Fox et al., Organometallics 13 (1994) 635.
J. Mol. Catal. A 213 (2004) 39.
A. Rouhi, Chem. & Eng. News 80 (51), Dec. 23, 2002, p. 29.
A. Katritsky et al., J. Org. Chem. 66 (2001) 5606.
T. Aoyama et al., Tetrahedron Lett. 21 (1980) 4461 (abstract).
J. Cesar et al., Tetrahedron Lett. 42 (2001) 7099 (abstract).
International Search Report and Written Opinion of the International Searching Authority, mailed in PCT/US2014/20890 on Oct. 22, 2014, 15 pages.
R. Subbarao et al., Indian J. Technol. 4 (1966) 153.
G. Cho et al., J. Ind. Eng. Chem. 3 (1997) 29.
G. Djigoue et al., Appl. Catal. A 368 (2009) 158.
P. Berger, Inform 21(9) (2010) 542.
D. Ogunniyi, Bioresource Technol. 97 (2006) 1086.
D. Zope, Inform 21(3) (2010) 186.
W. Rigby, J. Chem. Soc. (1956) 2560.
A. Hall et al., J. Organometal. Chem. 691 (2006) 5431.
Singapore Written Opinion and Search Report issued Jul. 26, 2016 from IPOS in corresponding SG Application No. 11201507218Q, 8 pages.

* cited by examiner

SURFACTANTS BASED ON MONOUNSATURATED FATTY ALCOHOL DERIVATIVES

FIELD OF THE INVENTION

The invention relates to surfactants, and in particular to monounsaturated fatty alcohol derivatives useful therein.

BACKGROUND OF THE INVENTION

Fatty alcohol derivatives, particularly alkoxylates, sulfates, and ether sulfates, are versatile surfactants. They are used across a broad array of industries and end uses, including personal care, laundry and cleaning, emulsion polymerization, agricultural uses, oilfield applications, industrial compositions, and specialty foamers.

Fatty alcohols are usually made by reducing the corresponding fatty acids or esters, typically by catalytic hydrogenation. Often, the catalyst includes zinc or copper and chromium. U.S. Pat. No. 5,672,781, for instance, uses a $CuCrO_4$ catalyst to hydrogenate methyl esters from palm kernel oil, which has substantial unsaturation, to produce a mixture of fatty alcohols comprising about 52 wt. % of oleyl alcohol, a monounsaturated fatty alcohol. For additional examples, see U.S. Pat. Nos. 2,865,968; 3,193,586; 4,804,790; 6,683,224; and 7,169,959.

The fatty acids or esters used to make fatty alcohols and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids.

Among fatty alcohols with internal unsaturation, oleyl alcohol has been used as a starting material to make ether sulfonates that have surfactant properties (see, e.g., U.S. Pat. Nos. 7,427,588 and 7,629,299).

Monounsaturated feedstocks having reduced chain length have potential value for making surfactants, but the feeds have not been readily available. Recent improvements in metathesis chemistry (see, e.g., J. C. Mol, *Green Chem.* 4 (2002) 5 and U.S. Pat. Appl. Publ. Nos. 2010/0145086, 2011/0113679, and 2012/0071676) will soon make such reduced chain unsaturated feedstocks available, but alternatives are needed.

Undecylenic acid (10-undecenoic acid) is produced industrially along with heptaldehyde by pyrolyzing the ricinoleic acid in castor oil (see U.S. Pat. No. 1,889,348; *J. Chem. Ed.* 29 (1952) 446; *J. Sci. Ind. Res.* 13B (1954) 277; and *J. Am. Oil Chem. Soc.* 66 (1989) 938). It is used primarily to manufacture pharmaceuticals, fragrances, and cosmetics.

Undecylenic acid is easily reduced to undecylenic alcohol with hydride reducing agents (e.g., lithium aluminum hydride) or selective hydrogenation catalysts (see, e.g., *J. Am. Chem. Soc.* 59 (1937) 1. It is known to ethoxylate undecylenic alcohol for possible use in laundry detergents (JP 10140195). Undecylenic alcohol ethoxylates have also been studied as principal components of self-assembled monolayers, which can mimic membrane structure and function (see, e.g., U.S. Pat. No. 6,809,196 and *J. Am. Chem. Soc.* 113 (1991) 12).

Undecylenic alcohol has been converted to sodium 10-undecenyl sulfate, and this compound has been used as a monomer for making polymerizable surfactants (see, e.g., *Electrophoresis* 25 (2004) 622; *New J. Chem.* 16 (1992) 883; and *Langmuir* 9 (1993) 2949).

Sulfation of alcohols produces alcohol sulfates, which have an C—O—$SO_3$X group, where X is typically an alkali metal or ammonium ion from a subsequent neutralization step. Sulfonation of unsaturated hydrocarbons gives sulfonates, which have a C—$SO_3$X group. When an unsaturated alcohol is the starting material, the unsaturated sulfate can be produced under some conditions (see, e.g., WO91/13057). With other reagents, alcohol sulfation and carbon-carbon double bond sulfonation may compete, with most of the reaction product resulting from sulfation, although the nature of the sulfonated by-products is generally not well understood (see, e.g., U.S. Pat. No. 5,446,188). Because of the competing side reactions, unsaturated alcohols are usually avoided when the goal is to make an alcohol sulfate or ether sulfate.

In sum, despite the known value of longer-chain fatty alcohols and shorter-chain saturated fatty alcohols for making ethoxylates, sulfates, and ether sulfates for use as surfactants, it is less clear what value the surfactants would have if they were made using shorter-chain unsaturated (e.g., $C_{10}$-$C_{12}$) fatty alcohols. The availability of undecylenic acid and undecylenic alcohol as feedstocks invites further investigation.

SUMMARY OF THE INVENTION

In one aspect, the invention relates to a composition comprising water and 1 to 99 wt. % of a surfactant. The surfactant comprises an alkoxylate, a sulfate or an ether sulfate of a $C_{10}$-$C_{12}$ monounsaturated alcohol. In particular aspects, the alkoxylate, sulfate, or ether sulfate derives from readily available undecylenic acid or undecylenic alcohol. In other aspects, the surfactant comprises 40 to 60 wt. % of a monounsaturated $C_{10}$-$C_{12}$ primary alcohol sulfate and 40 to 60 wt. % of a secondary hydroxyalkyl $C_{10}$-$C_{12}$ primary alcohol sulfate.

We found that alkoxylate, sulfate, and ether sulfate surfactants made from $C_{10}$-$C_{12}$ monounsaturated alcohols offer unexpected advantages. Compared with their saturated analogs, the monounsaturated alkoxylates, sulfates, and ether sulfates are less irritating, making them valuable for personal care, laundry, cleaners, and other household applications. Additional advantages are apparent from microscopy studies, which indicate that the monounsaturated alkoxylates, sulfates, and ether sulfates have favorable phase behavior over a wide range of actives levels. This enables formulation of products with greater compaction, allowing formulators to ship more product and less water in a given container. When combined with cationic surfactants, the alkoxylates, sulfates and ether sulfates exhibit considerable synergy, and they have improved solubility compared with their saturated analogs.

The surfactants will be useful in many applications and industries, including personal care, laundry and cleaning, emulsion polymerization, agricultural products, oilfield applications, and specialty foams.

DETAILED DESCRIPTION OF THE INVENTION

In one aspect, the invention relates to a composition comprising water and 1 to 99 wt. % of a surfactant. The surfactant comprises an alkoxylate, a sulfate or an ether sulfate of a $C_{10}$-$C_{12}$ monounsaturated alcohol. Preferably, the composition comprises 2 to 98 wt. % of the surfactant. More preferably, the composition comprises 5 to 95 wt. % of the surfactant.

As used herein, "monounsaturated" refers to compositions that comprise principally species having a single carbon-carbon double bond but may also include a minor proportion of one or more species that have two or more carbon-carbon double bonds. The skilled person will appreciate that it is not necessary and may be impractical to produce a purely "monounsaturated" species, and that mixtures comprising principally (but not exclusively) monounsaturated alcohols and their alkoxylate, sulfate, and ether sulfate derivatives are contemplated as within the scope of the invention.

The alkoxylates, sulfates, and ether sulfates derive from a $C_{10}$-$C_{12}$ monounsaturated alcohol. The unsaturation can be terminal or internal. Preferably, the alcohol is a primary alcohol. Thus, suitable $C_{10}$ monounsaturated alcohols include 9-decen-1-ol, 8-decen-1-ol, 7-decen-1-ol, 6-decen-1-ol, 5-decen-1-ol, 4-decen-1-ol, and 3-decen-1-ol. Suitable $C_{11}$ monounsaturated alcohols include 10-undecen-1-ol, 9-undecen-1-ol, 8-undecen-1-ol, 7-undecen-1-ol, 6-undecen-1-ol, 5-undecen-1-ol, 4-undecen-1-ol, and 3-undecen-1-ol. Suitable $C_{12}$ monounsaturated alcohols include 11-dodecen-1-ol, 10-dodecen-1-ol, 9-dodecen-1-ol, 8-dodecen-1-ol, 7-dodecen-1-ol, 6-dodecen-1-ol, 5-dodecen-1-ol, 4-dodecen-1-ol, and 3-dodecen-1-ol.

Other surfactant components may be present in addition to the alkoxylate, sulfate, or ether sulfate of the $C_{10}$-$C_{12}$ monounsaturated alcohol. Preferably, however, the surfactant comprises at least 10 wt. %, more preferably at least 20 wt. %, and most preferably at least 50 wt. %, of the alkoxylate, sulfate, or ether sulfate of the $C_{10}$-$C_{12}$ monounsaturated alcohol.

Undecylenic acid, because of its ready availability, is a preferred starting material for making many of the unsaturated alcohols, particularly undecylenic alcohol. Reduction of the acid or its ester derivatives using catalytic hydrogenation (see J. Am. Chem. Soc. 59 (1937) 1) or hydride reducing agents such as lithium aluminum hydride or the like provides undecylenic alcohol (10-undecen-1-ol).

Other $C_{11}$ monounsaturated alcohols having an internal carbon-carbon double bond can be made by isomerizing undecylenic alcohol to more-substituted olefins, typically using a base catalyst (see, e.g., Synthesis (1969) 97). Isomerization normally affords a mixture of monounsaturated alcohols, which may be desirable from a cost and/or performance perspective.

When $C_{10}$-$C_{12}$ monounsaturated alcohols having the carbon-carbon double bond in a particular location are needed, the Wittig reaction (see, e.g., Angew. Chem., Int. Ed. Engl. 4 (1965) 830; Tetrahedron Lett. 26 (1985) 307; and U.S. Pat. No. 4,642,364) can be used. The choice of starting materials for the Wittig reaction will depend on availability of starting materials. In one approach, an ω-hydroxyaldehyde and a phosphonium ylide (from the reaction of an alkyl halide and triphenylphosphine to give a phosphonium salt, followed by deprotonation to give the ylide) are used:

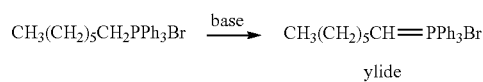

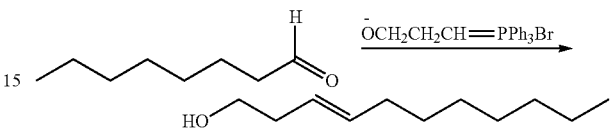

In another approach, an aldehyde and a phophonium ylide prepared from an ω-hydroxy alkyl halide are used:

4-Hydroxybutanal, which is produced in the manufacture of 1,4-butanediol, can be reacted with the phosphonium ylide reagent from a $C_6$, $C_7$, or $C_8$ alkyl halide to make, respectively, 4-decen-1-ol, 4-undecen-1-ol, or 4-dodecen-1-ol.

The Wittig reaction can also be used to produce terminally unsaturated alcohols, e.g., with reagents such as triphenylphosphonium methylide. In some cases, however, it may be more desirable to generate terminally unsaturated alcohols in another way. For instance, reaction of an α,ω-diol with a suitable dehydrating agent (e.g., $Ba_2P_2O_7$, HMPA, or even a fatty acid) can provide good yields of terminally unsaturated alcohols (see, e.g., J. Org. Chem. 36 (1971) 3826 and U.S. Pat. Nos. 4,250,343; 4,288,642; 4,447,659; 4,695,661, and 5,981,812, the teachings of which are incorporated herein by reference).

Ester precursors to terminally unsaturated alcohols are also available from metathesis chemistry. As an example, cross-metathesis of unsaturated fatty esters with ethylene can be used to generate terminally unsaturated $C_{10}$-$C_{12}$ unsaturated esters. Reduction of the esters provides the terminally unsaturated $C_{10}$-$C_{12}$ alcohol. For instance, cross-metathesis of methyl oleate and ethylene provides 1-decene and methyl 9-decenoate. The ester can be reduced to 9-decen-1-ol (see, e.g., U.S. Pat. No. 4,545,941, the teachings of which are incorporated by reference, and references cited therein). See also J. Org. Chem. 46 (1981) 1821; J. Catal. 30 (1973) 118; Appl. Catal. 70 (1991) 295; Organometallics 13 (1994) 635; Olefin Metathesis and Metathesis Polymerization by Ivin and Mol (1997), and Chem. & Eng. News 80(51), Dec. 23, 2002, p. 29, which also disclose useful metathesis catalysts.

In other aspects, undecylenic acid is used for the production of a $C_{10}$ monounsaturated alcohol. In one approach, the terminal carbon-carbon double bond is ozonized to give an aldehyde in which the chain length is reduced by one carbon. Reduction to a diol, followed by dehydration as described above provides 9-decen-1-ol.

In other aspects, undecylenic acid is used for the production of a $C_{12}$ monounsaturated alcohol. In one approach, the carboxylic acid group is homologated (see, e.g., J. Org. Chem. 66 (2001) 5606 and Tetrahedron Lett. 21 (1980) 4461; 42 (2001) 7099), and the resulting unsaturated carboxylic acid is reduced to give 11-dodecen-1-ol. In another approach, undecylenic alcohol is hydroformylated, and the resulting aldehyde (or aldehyde mixture) is hydrogenated to give a diol. The diol is then dehydrated to give 11-dodecen-1-ol as the major product.

In other aspects, the monounsaturated alcohol or alcohol precursor (e.g., a fatty acid or ester) is generated using a microorganism or bioengineered microorganism, such as an algae, bacterium, or yeast-based microbe.

Reduction of monounsaturated ester or acid precursors to produce the $C_{10}$-$C_{12}$ monounsaturated alcohols is performed using well-known catalysts and procedures. The reducing agent is typically either a hydride reducing agent (sodium borohydride, lithium aluminum hydride, or the like) or molecular hydrogen in combination with a metal catalyst, frequently copper and/or zinc in combination with chromium (see, e.g., U.S. Pat. Nos. 2,865,968; 3,193,586; 4,804,790; 5,124,491; 5,672,781; 6,683,224; 7,169,959 and 7,208,643, the teachings of which are incorporated herein by reference).

The skilled person will appreciate that the reduction process, particularly when transition metal catalysts are used to convert precursors to alcohols, can induce some degree of isomerization or migration of the carbon-carbon double bond from its original position. Moreover, because hydrogenation catalysts are not always completely selective, a proportion of the carbon-carbon double bonds might be hydrogenated during the ester or acid reduction, resulting in a mixed product that may have saturated $C_{10}$-$C_{12}$ fatty alcohols in addition to the desired unsaturated $C_{10}$-$C_{12}$ fatty alcohols. The skilled person can control the degree of unsaturation to any desired amount.

The skilled person will, of course, recognize other desirable ways to arrive at the $C_{10}$-$C_{12}$ monounsaturated alcohols used to produce the inventive alkoxylate, sulfate, and ether sulfate-based compositions.

Monounsaturation can also impart advantages to formulated products (including consumer products) that are often not available with the corresponding saturated fatty alcohol derivatives. Because crystallinity is disrupted by the presence of a carbon-carbon double bond, monounsaturated alkoxylates, sulfates, and ether sulfates usually have lower viscosities than their saturated analogs. Moreover, the monounsaturated alkoxylates, sulfates, and ether sulfates can be concentrated and formulated at higher actives levels—sometimes much higher—than their saturated counterparts. For instance, a saturated ether sulfate might allow a maximum 30 wt. % actives level to give a flowable liquid, whereas an otherwise similar monounsaturated ether sulfate could allow the actives level to be as high as 70 or 80 wt. %. Thus, the seemingly minor structural change to a monounsaturated product can enable shipment of more concentrated products, reduce or eliminate the need for special handling equipment, and/or ultimately provide substantial cost savings. The monounsaturated alkoxylates, sulfates, and ether sulfates are also more effective as compatibilizers for surfactants or other components in the fully formulated products.

The inventive alkoxyaltes, sulfates, or ether sulfates are made by alkoxylating, sulfating, or alkoxylating (preferably ethoxylating) and sulfating the monounsaturated $C_{10}$-$C_{12}$ alcohol compositions using well-known techniques.

For instance, the unsaturated $C_{10}$-$C_{12}$ alcohol can be alkoxylated by reacting it with ethylene oxide, propylene oxide, or a combination thereof to produce an alkoxylate. Alkoxylations are usually catalyzed by a base (e.g., KOH), but other catalysts such as double metal cyanide complexes (see, e.g., U.S. Pat. No. 5,482,908) can also be used. The oxyalkylene units can be incorporated randomly or in blocks. A series of products with different degrees of alkoxylation can be easily produced using a single reactor. This is illustrated in the examples below in the sequential ethoxylation of undecylenic alcohol to produce ethoxylates having, on average, 1, 3, or 7 moles of oxyethylene units per mole of unsaturated $C_{10}$-$C_{12}$ alcohol starter.

The unsaturated $C_{10}$-$C_{12}$ alcohol can be sulfated, with or without a prior alkoxylation, and if applicable, neutralized to give a monounsaturated alkyl sulfate or a monounsaturated alkyl ether sulfate according to known methods (see, e.g., U.S. Pat. No. 3,544,613, the teachings of which are incorporated herein by reference). Sulfamic acid is a convenient reagent that sulfates the hydroxyl group without disturbing the unsaturation. Thus, warming the monounsaturated alcohol or alkoxylate with sulfamic acid optionally in the presence of urea or another proton acceptor conveniently provides the desired $C_{10}$-$C_{12}$ monounsaturated alkyl ammonium sulfate or ether sulfate (see examples below). The ammonium sulfate is easily converted to an alkali metal sulfate by reaction with an alkali metal hydroxide or other ion-exchange reagents. In the examples below, monounsaturated alkyl sodium sulfates are prepared from the corresponding ammonium sulfates by reacting the latter with aqueous sodium hydroxide.

Other reagents can be used to convert hydroxyl groups of a $C_{10}$-$C_{12}$ unsaturated alcohol or alkoxylate to sulfates. For instance, sulfur trioxide, oleum, or chlorosulfonic acid may be used. Some of these reagents can, under the right conditions, also react with the unsaturation to form a sulfonate (having a carbon-sulfur bond), which may or may not be the desired outcome. Sulfur trioxide, for instance, can be used to sulfate the hydroxyl group of an unsaturated alcohol or alkoxylate, but it may also react with a carbon-carbon double bond to generate a β-sultone, which can ring open to give mixtures of hydroxyalkane sulfonates and alkene sulfonates. Thus, it is possible, and may be desirable, to perform both sulfation and sulfonation in one pot, and often with a single reagent. A product having at least some proportion of material that is both sulfonated and sulfated might be desirable. For instance, a combined sulfate/sulfonate can impart beneficial properties to the bulk surfactant, including reduced viscosity, better concentratability, better compatibilizing properties, or other advantages.

The invention includes processes for making alkoxylates, sulfates, and ether sulfates of $C_{10}$-$C_{12}$ monounsaturated alcohols. The processes comprise reacting a composition comprising a $C_{10}$-$C_{12}$ monounsaturated alcohol with an alkoxylating agent, a sulfating agent, or an alkoxylating agent followed by a sulfating agent, to make, respectively, an alkoxylate, a sulfate, or an ether sulfate. Thus, one suitable process comprises sulfating the monounsaturated $C_{10}$-$C_{12}$ alcohol composition to give an alkyl sulfate. Another suitable process comprises alkoxylating the $C_{10}$-$C_{12}$ alcohol composition with one or more alkylene oxides, preferably ethylene oxide, to give a monounsaturated alkoxylate, followed by sulfation to give a monounsaturated alkyl ether sulfate.

As discussed earlier, the inventive surfactant compositions comprise water and 1 to 99 wt. % of a surfactant comprising an alkoxylate, a sulfate, or an ether sulfate of a $C_{10}$-$C_{12}$ monounsaturated alcohol. In one aspect, the surfactant comprises: (a) 40 to 60 wt. % of a monounsaturated $C_{10}$-$C_{12}$ primary alcohol sulfate; and (b) 40 to 60 wt. % of a secondary hydroxyalkyl $C_{10}$-$C_{12}$ primary alcohol sulfate. Preferably, the surfactant comprises 45 to 55 wt. % of the monounsaturated $C_{10}$-$C_{12}$ primary alcohol sulfate; and 45 to 55 wt. % of the secondary hydroxyalkyl $C_{10}$-$C_{12}$ primary alcohol sulfate. The sulfate composition may further comprise 0.1 to 20 wt. %, preferably 0.5 to 15 wt. %, of sulfonated products.

Although sulfation and sulfonation are known to compete when an unsaturated fatty alcohol is the starting material, we surprisingly found that certain sulfation conditions, such as falling-film sulfation using sulfur trioxide, can provide roughly equal amounts of (a) a monounsaturated $C_{10}$-$C_{12}$ primary alcohol sulfate and (b) a secondary hydroxyalkyl $C_{10}$-$C_{12}$ primary alcohol sulfate. Without wishing to be bound to any particular theory, we believe that the products may result from formation of an intermediate dialkylsulfate. Upon neutralization of the acid, the dialkylsulfate may undergo both elimination, to revert back to the unsaturated $C_{10}$-$C_{12}$ alcohol sulfate, as well as hydrolysis to afford the hydroxyalkyl alcohol sulfate (see scheme below). The hydrolysis appears to be selective, providing preferentially the secondary alcohol and the primary alcohol sulfate. Consequently, the product mixture from reaction of a $C_{10}$-$C_{12}$ monounsaturated alcohol, particularly one that is not ethoxylated, typically comprises about 90% sulfates—with roughly equal amounts of monounsaturated $C_{10}$-$C_{12}$ primary alcohol sulfate and $C_{10}$-$C_{12}$ secondary hydroxyalkyl alcohol sulfate—and about 10% sulfonated products. As illustrated for a $C_{12}$ monounsaturated alcohol:

ammonium or substituted ammonium cation. Preferably, R is a linear $C_{10}$-$C_{12}$ monounsaturated hydrocarbyl group.

We found that falling-film sulfation with sulfur trioxide tends to scramble carbon-carbon double bond geometry. Thus, the product mixture frequently approaches a thermodynamically preferred mixture of cis- and trans-isomers, usually about 8:2 trans-/cis-, even if the unsaturation in the unsaturated $C_{10}$-$C_{12}$ alcohol was predominantly or exclusively cis- or trans-.

In other preferred aspects, the secondary hydroxyalkyl $C_{10}$-$C_{12}$ primary alcohol sulfate has the structure:

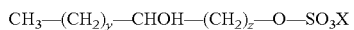

wherein y=0 to 8, z=0 to 8, y+z=8 to 10, and X is a mono- or divalent cation or an ammonium or substituted ammonium cation. Preferably, y+z=9.

The sulfate compositions are preferably made by sulfating a monounsaturated $C_{10}$-$C_{12}$ alcohol with sulfur trioxide in a falling-film reactor, followed by neutralization, according to methods described earlier.

We also found that terminal unsaturation is not retained when sulfur trioxide is used to make monounsaturated

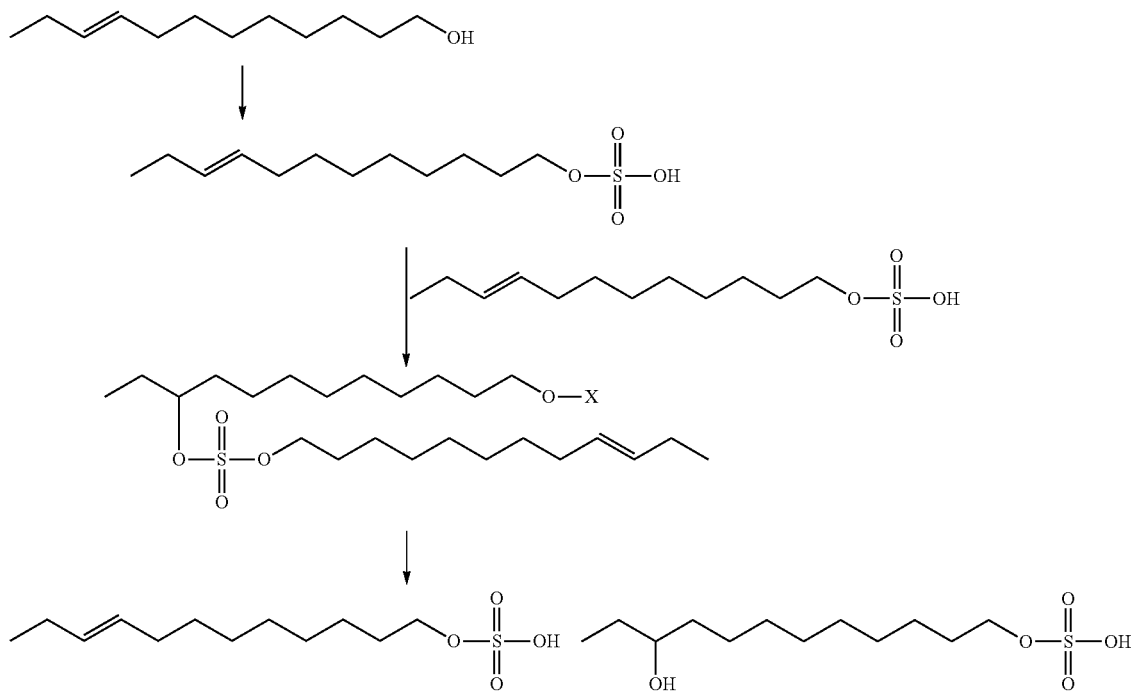

In contrast, when ethoxylated $C_{10}$-$C_{12}$ alcohols are subjected to falling-film sulfation with sulfur trioxide, the unsaturated ether sulfate predominates. For instance, an ethoxylate from 1 mole of EO gives about 70% unsaturated ether sulfate, and a 3 mole ethoxylate gives about 80% unsaturated ether sulfate (see examples below).

In a preferred aspect, the monounsaturated $C_{10}$-$C_{12}$ primary alcohol sulfate and the secondary hydroxyalkyl $C_{10}$-$C_{12}$ primary alcohol sulfate derive from undecylenic alcohol.

In some preferred compositions, the monounsaturated $C_{10}$-$C_{12}$ primary alcohol sulfate has the structure:

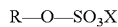

wherein R is a linear or branched $C_{10}$-$C_{12}$ monounsaturated hydrocarbyl group, and X is a mono- or divalent cation or an $C_{10}$-$C_{12}$ alcohol sulfates and ether sulfates. Instead, isomerization occurs to give more-substituted unsaturated products. Thus, in one inventive process, an internally monounsaturated $C_{10}$-$C_{12}$ alcohol sulfate or ether sulfate is made. This process comprises reacting a terminally monounsaturated $C_{10}$-$C_{12}$ alcohol or alkoxylate with sulfur trioxide in a falling-film reactor, followed by neutralization.

We also observed positional isomerization upon sulfation of internally unsaturated $C_{10}$-$C_{12}$ alcohols. This may occur through the regeneration of an olefin when a dialkylsulfate eliminates in the "opposite" direction (or side of the chain) from which the addition had occurred. Whether or not the olefin can fully "zip" up and down the chain is unclear. Positional isomerization could occur by multiple addition/ elimination, olefin migration prior to addition of the sulfuric acid ester, or some other mechanism.

The alkoxylate, sulfate, or ether sulfate-based surfactant compositions may be incorporated into various formulations and used as emulsifiers, skin feel agents, film formers, rheological modifiers, solvents, release agents, biocides, biocide potentiators, conditioners, dispersants, hydrotropes, or the like. Such formulations may be used in end-use applications including, among others: personal care; household, industrial, and institutional cleaning products; oilfield applications; enhanced oil recovery; gypsum foamers; coatings, adhesives and sealants; and agricultural formulations.

Thus, the alkoxylates, sulfates, or ether sulfates may be used in such personal care applications as bar soaps, bubble baths, liquid cleansing products, conditioning bars, oral care products, shampoos, body washes, facial cleansers, hand soaps/washes, shower gels, wipes, baby cleansing products, creams/lotions, hair treatment products, antiperspirants, and deodorants.

Cleaning applications include, among others, household cleaners, degreasers, sanitizers and disinfectants, liquid and powdered laundry detergents, heavy duty liquid detergents, light-duty liquid detergents, hard and soft surface cleaners for household, autodish detergents, rinse aids, laundry additives, carpet cleaners, spot treatments, softergents, liquid and sheet fabric softeners, industrial and institutional cleaners and degreasers, oven cleaners, car washes, transportation cleaners, drain cleaners, industrial cleaners, foamers, defoamers, institutional cleaners, janitorial cleaners, glass cleaners, graffiti removers, concrete cleaners, metal/machine parts cleaners, and food service cleaners.

In specialty foam applications (firefighting, gypsum, concrete, cement wallboard), the alkoxylates, sulfates, or ether sulfates function as foamers, wetting agents, and foam control agents.

In paints and coatings, the alkoxylates, sulfates, or ether sulfates are used as solvents, coalescing agents, or additives for emulsion polymerization.

In oilfield applications, the alkoxylates, sulfates or ether sulfates can be used for oil and gas transport, production, stimulation, enhanced oil recovery, and as components of drilling fluids.

In agricultural applications, the alkoxylates, sulfates, or ether sulfates are used as solvents, dispersants, surfactants, emulsifiers, wetting agents, formulation inerts, or adjuvants.

As demonstrated in the examples below, the inventive alkoxylate, sulfate, or ether sulfate-based compositions are exceptionally useful in applications requiring low irritation, agricultural dispersants, water-soluble herbicides, aqueous hard surface cleaner degreasers and glass cleaners, and surfactant applications that require high actives levels or improved solubility.

Preparation of Sulfates and Ether Sulfates from Undecylenic Alcohol

Undecylenic Alcohol Sulfate, Sodium Salt

A large-scale, water-jacketed (40° C.) batch reactor equipped with addition funnel, mechanical stirring, and nitrogen inlet (5 mL/min. flow rate) is charged with undecylenic alcohol (125.5 g, 0.737 mol). Sulfur trioxide (70.7 g, 1.2 eq.) is charged to the addition funnel, then added carefully to the vaporizer while maintaining the reaction temperature below 50° C. Initial fuming in the headspace is severe. Following the $SO_3$ addition, the reactor is purged with nitrogen for 5 min. Total addition time: 2 h, 15 min. The acid intermediate is dark brown with moderate viscosity.

A round-bottom flask equipped with mechanical stirring is charged with water (418.4 g) and sodium hydroxide solution (61.6 g of 50% aq. NaOH). The acid intermediate from above (160.0 g) is added to the aqueous base solution, and the resulting mixture is heated to and held at 70° C. for 1 h. The product is filtered to remove particulates. $^1$H NMR analysis shows migration of the carbon-carbon double bond and about 44% of monounsaturated $C_{11}$ primary alcohol sulfate. Solids: 28.1%; unsulfated alcohol: 0.46%; inorganic sulfate: 0.24%; actives: 27.4%. Yield: 167.4 g (91%).

1-Undecanol Sulfate, Sodium Salt

The procedure described above is followed to prepare the saturated $C_{11}$ alcohol sulfate from 1-undecanol (125.1 g) and sulfur trioxide (71.9 g, 1.2 eq.). Total addition time for the sulfur trioxide: 1.5 h. The acid is dark brown with low viscosity.

Conversion to the sodium sulfate is performed using water (471.3 g), sodium hydroxide solution (68.7 g of 50% aq. NaOH), and the acid intermediate (180.0 g). The acid is added while keeping the reaction temperature below 50° C., and the resulting product is mixed for 1 h. The pH is adjusted to 8.6 with 10% aq. $H_2SO_4$ solution, and the product is transferred to a jar. Solids: 24.9%; unsulfated alcohol: 1.27%; inorganic sulfate: 2.45%; actives: 21.2%. Yield: 190 g (100%).

Ethoxylation of Undecylenic Alcohol to Produce 1, 3, and 7 Mole Alcohol Ethoxylates Ethoxylations are performed sequentially using one reactor to prepare undecylenic alcohol ethoxylates that have, on average, 1, 3, or 7 oxyethylene units.

Undecylenic alcohol (1796 g) is charged to a pressure reactor. Liquid KOH (45%, 17.6 g) is added. The reactor is sealed and heated to 100° C. under nitrogen with agitation. At ~50° C., vacuum (20 mm) is applied to remove water. The contents are further heated to 105-115° C. under vacuum (20 mm) and held for 3 h with a nitrogen sparge.

The remaining dried catalyzed alcohol feed (1802 g) is heated to 145° C. The reactor is pressurized with nitrogen and vented three times. Ethylene oxide (460 g, 1 mole per mole of starter) is introduced to the reactor at 145-160° C. over 1 h. After the EO addition, the mixture digests for 1 h at 150-160° C. until the reactor pressure equilibrates. The mixture is cooled to 50° C. and partially drained (380 g removed) to provide the 1 mole ethoxylated unsaturated alcohol. Hydroxyl value: 259 mg KOH/g; iodine value: 149 g $I_2$/100 g sample.

The reactor contents (1880 g) are re-heated to 145° C., and the reactor is vented with nitrogen as described earlier. Ethylene oxide (775 g, 2 additional moles per mole of starter; 3 moles of EO per mole of undecylenic alcohol charged) is added to the feed at 145-160° C. After digesting 1 h at 150-160° C., the mixture is cooled to 60° C. and partially drained (470 g removed) to recover the 3 mole ethoxylated unsaturated alcohol. Hydroxyl value: 183 mg KOH/g; iodine value: 149 g $I_2$/100 g sample.

The reactor contents (2185 g) are re-heated to 145° C., and the reactor is vented with nitrogen as described earlier. Ethylene oxide (1265 g, 4 additional moles per mole of starter; 7 moles of EO per mole of undecylenic alcohol charged) is added to the feed at 145-160° C. After digesting 1 h at 150-160° C., the mixture is cooled to 60° C. and drained to recover the 7 mole ethoxylated unsaturated alcohol. Hydroxyl value: 116 mg KOH/g; iodine value: 52 g $I_2$/100 g sample. Yield: 3450 g.

Ethoxylation of 1-Undecanol to Produce 1, 3, and 7 Mole Alcohol Ethoxylates

Ethoxylations are performed sequentially using one reactor to prepare 1-undecanol ethoxylates that have, on average, 1, 3, or 7 oxyethylene units.

1-Undecanol (1715 g) is charged to a pressure reactor. Liquid KOH (45%, 18.0 g) is added. The reactor is sealed and heated to 100° C. under nitrogen with agitation. At ~50° C., vacuum (20 mm) is applied to remove water. The contents are further heated to 105-115° C. under vacuum (20 mm) and held for 3 h with a nitrogen sparge.

The remaining dried catalyzed alcohol feed (1713 g) is heated to 145° C. The reactor is pressurized with nitrogen and vented three times. Ethylene oxide (440 g, 1 mole per mole of starter) is introduced to the reactor at 145-160° C. over 1 h. After the EO addition, the mixture digests for 1 h at 150-160° C. until the reactor pressure equilibrates. The mixture is cooled to 50° C. and partially drained (299 g removed) to provide the 1 mole ethoxylated saturated alcohol. Hydroxyl value: 257 mg KOH/g.

The reactor contents (1854 g) are re-heated to 145° C., and the reactor is vented with nitrogen as described earlier. Ethylene oxide (750 g, 2 additional moles per mole of starter; 3 moles of EO per mole of 1-undecanol charged) is added to the feed at 145-160° C. After digesting 1 h at 150-160° C., the mixture is cooled to 60° C. and partially drained (407 g removed) to recover the 3 mole ethoxylated saturated alcohol. Hydroxyl value: 184 mg KOH/g.

The reactor contents (2197 g) are re-heated to 145° C., and the reactor is vented with nitrogen as described earlier. Ethylene oxide (1275 g, 4 additional moles per mole of starter; 7 moles of EO per mole of 1-undecanol charged) is added to the feed at 145-160° C. After digesting 1 h at 150-160° C., the mixture is cooled to 60° C. and drained to recover the 7 mole ethoxylated saturated alcohol. Hydroxyl value: 116 mg KOH/g. Yield: 3472 g.

Preparation of Ether Sulfates
Undecylenic Alcohol, 1 EO Ether Sulfate, Sodium Salt The procedure used for undecylenic alcohol is generally followed using undecylenic alcohol 1EO ethoxylate (123.5 g, 0.578 mol) and sulfur trioxide (55.5 g, 0.693 mol, 1.2 eq.). Total addition time: 1 h, 50 min. The acid intermediate (155.0 g) is combined with water (414.3 g) and aqueous sodium hydroxide solution (50.7 g of 50% NaOH) and heated 1 h at 70° C. $^1$H NMR analysis indicates 57% internal olefin and 13% terminal olefin present. Solids: 28.0%; unsulfated alcohol: 0.97%; inorganic sulfate: 0.14%; actives: 26.9%. Yield: 162.0 g (95%).

1-Undecanol, 1EO Ether Sulfate, Sodium Salt

The procedure used for undecylenic alcohol is generally followed using 1-undecanol 1EO ethoxylate (123.2 g, 0.564 mol) and sulfur trioxide (53.9 g, 0.674 mol, 1.2 eq.). Total addition time: 1 h, 35 min. The acid intermediate (160.0 g) is combined with water (428.5 g) and aqueous sodium hydroxide solution (51.5 g of 50% NaOH) and heated 1 h at 70° C. Solids: 27.4%; unsulfated alcohol: 0.76%; inorganic sulfate: 0.52%; actives: 26.2%. Yield: 165.4 g (98%).

Undecylenic Alcohol, 3EO Ether Sulfate, Sodium Salt

The procedure used for undecylenic alcohol is generally followed using undecylenic alcohol 3EO ethoxylate (118.9 g, 0.393 mol) and sulfur trioxide (37.6 g, 0.469 mol, 1.2 eq.). Total addition time: 1 h, 30 min. The acid intermediate (140.0 g) is combined with water (384.8 g) and aqueous sodium hydroxide solution (35.2 g of 50% NaOH) and heated 1 h at 70° C. $^1$H NMR analysis indicates 62% terminal olefin and 19% internal olefin present. Solids: 27.2%; unsulfated alcohol: 1.61%; inorganic sulfate: 0.13%; actives: 25.4%. Yield: 145.1 g (97%).

1-Undecanol, 3EO Ether Sulfate, Sodium Salt

The procedure used for undecylenic alcohol is generally followed using 1-undecanol 3EO ethoxylate (150.2 g, 0.493 mol) and sulfur trioxide (47.3 g, 0.591 mol, 1.2 eq.). Total addition time: 1 h, 25 min. The acid intermediate (180.0 g) is combined with water (495.1 g) and aqueous sodium hydroxide solution (44.9 g of 50% NaOH) and heated 1 h at 70° C. Solids: 26.8%; unsulfated alcohol: 1.09%; inorganic sulfate: 0.27%; actives: 25.5%. Yield: 186.4 g (98%).

Undecylenic Alcohol, 1 EO Ether Sulfate, Ammonium Salt

A four-neck flask equipped with overhead mechanical stirrer, condenser, nitrogen inlet, thermocouple, heating mantle, and temperature controller is charged with undecylenic alcohol 1EO ethoxylate (111 g, 0.520 mol) and 1,4-dioxane (250 mL). Sulfamic acid (53.0 g, 0.546 mol) and urea (1.64 g) are added. The mixture is heated to reflux (about 103° C.) for 4 h. Analysis by $^1$H NMR (MeOD) indicates ~99% conversion to sulfate. Upon cooling, the mixture becomes a slurry. Chloroform (500 mL) is added and the mixture is heated to 55° C. Upon cooling and standing overnight, very fine insolubles settle to bottom. The solution is vacuum filtered using filter aid and a coarse funnel, washing with fresh chloroform. The filtrate is concentrated by rotary evaporation. The dioxane-wet paste is then dissolved in methanol (500 mL), adjusted to ~pH 7 with ammonium hydroxide, and then reconcentrated. This procedure is repeated 5X, with the last concentration stopped before the product becomes too thick. Material is transferred to glass baking dish, using MeOH to quantitatively transfer residue. The solids are allowed to dry in a hood over the weekend and then further dried in a vacuum oven (70° C., 5 h). The product is a yellow semi-solid. $^1$H NMR analysis indicates 99% conversion to the ammonium sulfate.

1-Undecanol, 1 EO Ether Sulfate, Ammonium Salt

The procedure used above to convert undecylenic alcohol 1 EO ethoxylate to the ammonium sulfate is generally followed using 1-undecanol 1EO ethoxylate (109.5 g, 0.508 mol), sulfamic acid (51.8 g, 0.533 mol), 1,4-dioxane (250 mL), and urea (1.61 g). The product is a yellow semi-solid. $^1$H NMR analysis indicates quantitative conversion to the ammonium sulfate.

Evaluation of Alcohol Sulfates and Ether Sulfates in Product Development Applications
Zein Test The zein test is based on solubilization by surfactants of a yellow corn (maize) protein that is normally insoluble in water unless it is denatured. The test gravimetrically determines the amount of zein dissolved by a surfactant solution. The solubility of zein in surfactant solutions correlates well with skin irritation or roughness caused by the surfactant. The "zein number" is a value relative to a normalized control, i.e., a 1% actives solution of Stepanol® WA-Extra PCK (sodium lauryl sulfate) in water. A higher zein number corresponds to a greater degree of irritation.

A 1% actives solution of each test surfactant (120 mL) is prepared. The pH of each solution is adjusted to about 7.0 with dilute aq. sulfuric acid or dilute aq. sodium hydroxide. The surfactant solution is warmed to 45° C. Zein powder (1.50 g) is added to each of three jars. Surfactant (25.0 g of 1% actives solution) is added to each jar, and to one empty jar to be used as a blank. The solutions are mixed using magnetic stirring on a temperature-controlled hotplate at 45° C. for 60 min. Each mixture is then centrifuged (2500 rpm, 15 min.), and undissolved zein powder is isolated by vacuum filtration. The residue is washed with deionized water and dried (55° C., 24 h) to constant weight. The amount of undissolved zein protein is found gravimetrically, and the results from three runs are averaged to give the % of solubilized zein and zein number. Results appear in Table 1.

TABLE 1

Results of Zein Test[1]

| | % solubilized zein | zein number | comment |
|---|---|---|---|
| Stepanol ® WA-Extra PCK (SLS) | 49.6 | 100 | control |
| Unsat. $C_{11}$ alcohol Na sulfate | 9.6 | 19.3 | Unsaturated derivative is much less irritating than the saturated analog |
| Sat. $C_{11}$ alcohol Na sulfate | 52.9 | 107 | |
| Unsat. $C_{11}$ alcohol 1EO Na sulfate | 8.3 | 16.7 | Unsaturated derivative is much less irritating than the saturated analog |
| Sat. $C_{11}$ alcohol 1EO Na sulfate | 33.7 | 68.0 | |
| Unsat. $C_{11}$ alcohol 3EO Na sulfate | 16.5 | 31.6 | Unsaturated derivative is less irritating than the saturated analog |
| Sat. $C_{11}$ alcohol 3EO Na sulfate | 22.3 | 44.9 | |

[1]Average of three runs

As shown in Table 1, the sulfate and ether sulfate derivatives made from undecylenic alcohol are less or much less irritating than their saturated analogs based on the test results. All of the unsaturated derivatives tested are far less irritating when compared with the control, Stepanol® WA-Extra PCK (sodium lauryl sulfate). There appears to be less of a difference in the zein number between the unsaturated derivative and its saturated analog when the degree of ethoxylation is greater.

Hard-Surface Cleaners: Glass Cleaner

Control: Stepanol WA-Extra® SLS (sodium lauryl sulfate, 1.0 g, product of Stepan, 29.4% active) is combined with isopropyl alcohol (2.0 g) and diluted to 100 mL with deionized water.

Test Formulation: Test sample (1.2 to 1.4 g) is combined with isopropyl alcohol (2.0 g) and diluted to 100 mL with deionized water.

Test Materials:

Saturated $C_{11}$ alcohol sulfate, Na salt, 21.2% actives

Unsaturated $C_{11}$ alcohol sulfate, Na salt, 27.4% actives

Saturated $C_{11}$ alcohol 3EO ethoxylate sulfate, Na salt, 25.5% actives

Unsaturated $C_{11}$ alcohol 3EO ethoxylate sulfate, Na salt, 25.4% actives

Formulations:
A: Saturated Na sulfate (1.4 g). Clear, pH 4-5
B: Unsaturated Na sulfate (1.1 g). Clear, pH 9-10
C: Saturated 3EO Na sulfate (1.2 g). Clear, pH 6-7
D: Unsaturated 3EO Na sulfate (1.2 g). Clear, pH 7-8

Method: The test formulation is evaluated for clarity; only clear formulations are evaluated in the low film/low streak test. The test measures the ability of the cleaner to leave a streak and film-free surface on a test mirror. The test formula is applied to a mirror in a controlled quantity and wiped with a standard substrate back and forth, leaving the spread product to dry. Once dry, the mirrors are evaluated and rated by a two-person panel. Results appear in Table 2.

As shown in Table 2 (A versus B), the formulation based on the $C_{11}$ unsaturated alcohol sulfate, sodium salt (formulation B) outperforms formulation A, which is based on a $C_{11}$ saturated alcohol sulfate, sodium salt in terms of a reduced degree of streaking.

Comparing formulations C and D, both the unsaturated alcohol 3EO sulfate, sodium salt, and its saturated analog perform similarly and well in the test. Both perform nearly as well as the control in terms of a low degree of filming and streaking and both perform better when compared with the alcohol sulfate formulations (A & B).

TABLE 2

Glass Cleaner Performance

| A versus B | Observations | Filming on mirror panel | Streaking on mirror panel |
|---|---|---|---|
| Control | Clear; no film or streak | 0% | 0% |
| B-Unsat. $C_{11}$ alcohol Na sulfate | Slight streaking | 0% | 5% |
| A-Saturated $C_{11}$ alcohol Na sulfate | Unacceptable streaking | 0% | 30% |
| Better of A and B | B | | |

| C versus D | Observations | Filming on mirror panel | Streaking on mirror panel |
|---|---|---|---|
| Control | Clear; no film or streak | 0% | 0% |
| D-Unsaturated $C_{11}$ alcohol 3EO Na sulfate | Minimal spotting; almost equal to control | 0% | 1% |
| C-Saturated $C_{11}$ alcohol 3EO Na sulfate | Very minor streaking/spotting | 0% | 3% |
| Better of C and D | D | | |

Hard Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product.

Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (1.1 to 1.4 g), and deionized water (to 100.0 g solution). The control sample for anionic testing replaces the test sample with Stepanol® WA-Extra PCK (sodium lauryl sulfate, Stepan, 1.0 g, 29.4% active).

Test Materials:
Saturated $C_{11}$ alcohol sulfate, Na salt, 21.2% actives
Unsaturated $C_{11}$ alcohol sulfate, Na salt, 27.4% actives
Saturated $C_{11}$ alcohol 3EO ethoxylate sulfate, Na salt, 25.5% actives
Unsaturated $C_{11}$ alcohol 3EO ethoxylate sulfate, Na salt, 25.4% actives Formulations:
A: Saturated Na sulfate (1.4 g). Clear, pH 7.5
B: Unsaturated Na sulfate (1.1 g). Clear, pH 7.5
C: Saturated 3EO Na sulfate (1.2 g). Clear, pH 7.4
D: Unsaturated 3EO Na sulfate (1.2 g). Clear, pH 7.5

Soil Composition (from Gardner ASTM D4488-95 Method):

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica (18), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

Results appear in Table 3. As shown in the table, all of the test samples perform equal to the control within the limits of the test method.

TABLE 3

Gardner Straight-Line Washability Test

| | Ave. % clean after 2, 4, 6, 8, or 10 swipes | | | | | Rating |
|---|---|---|---|---|---|---|
| | 2 | 4 | 6 | 8 | 10 | |
| WA-Extra (sat $C_{12}$ Na sulfate) | 91.3 | 93.6 | 93.2 | 94.1 | 95.4 | control |
| Unsat $C_{11}$ alcohol Na sulfate | 92.5 | 94.4 | 94.9 | 95.2 | 96.2 | equal |
| Sat $C_{11}$ alcohol Na sulfate | 91.4 | 94.5 | 96.4 | 98.2 | 97.5 | equal |
| Unsat $C_{11}$ 3EO Na sulfate | 94.0 | 97.4 | 99.1 | 96.5 | 100 | equal |
| Sat $C_{11}$ 3EO Na sulfate | 97.5 | 98.9 | 98.9 | 99.3 | 100 | equal |

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. A standard dilution test is conducted whereby the concentrates are diluted in water to determine if solubility is complete.

Control: Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 4 below.

Anionic Test Sample: Paraquat (4.57 g of 43.8% active material) is added to a 20-mL glass vial. An eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample: Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample: Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Test Materials:
Saturated $C_{11}$ alcohol sulfate, Na salt, 21.2% actives
Unsaturated $C_{11}$ alcohol sulfate, Na salt, 27.4% actives
Saturated $C_{11}$ alcohol 1 EO ethoxylate sulfate, Na salt, 26.2% actives
Unsaturated $C_{11}$ alcohol 1EO ethoxylate sulfate, Na salt, 26.9% actives
Saturated $C_{11}$ alcohol 1 EO ethoxylate sulfate, $NH_4$ salt, 97.5% actives
Unsaturated $C_{11}$ alcohol 1EO ethoxylate sulfate, $NH_4$ salt, 95.5% actives
Saturated $C_{11}$ alcohol 3EO ethoxylate sulfate, Na salt, 25.5% actives
Unsaturated $C_{11}$ alcohol 3EO ethoxylate sulfate, Na salt, 25.4% actives Criteria for emulsion solubility: Test samples should be as good as or better than the control with no separation after one hour. All of the tested formulations perform well in comparison to the controls, particularly when the saturated or unsaturated $C_{11}$ alcohol derivative is used to replace the anionic portion of the formulation (left set of columns in Table 4). Overall, no significant difference is noted between the unsaturated $C_{11}$ alcohol derivatives and their saturated counterparts in this test. Results appear in Table 4.

TABLE 4

Water Soluble Herbicide Formulation: Emulsion stability, mL separation

| test sample | Anionic | | | Nonionic | | | Adjuvant | | | Rating |
|---|---|---|---|---|---|---|---|---|---|---|
| | sol | 1 h | 24 h | sol | 1 h | 24 h | sol | 1 h | 24 h | |
| Unsaturated Na sulfate | S | 0 | 0 | I | 0.25 | 0.4 | D | 0 | 0.25 | good |
| Saturated Na sulfate | S | 0 | 0 | I | 0.2 | 0.3 | I | 0.2 | 0.4 | good |
| Unsat. 1EO Na sulfate | S | 0 | 0 | D | 0.2 | 0.25 | D | 0 | 0.5 | good |
| Sat. 1EO Na sulfate | S | 0 | 0 | D | 0.2 | 0.5 | D | 0 | 0.2 | good |
| Unsat. 3EO Na sulfate | S | 0 | 0 | D | 0.2 | 0.5 | D | 0 | Tr | good |
| Sat. 3EO Na sulfate | S | 0 | 0 | D | 0.1 | 0.5 | D | 0 | Tr | good |
| Unsat. 1EO $NH_4$ sulfate | S | 0 | 0 | D | 0 | Tr | S | 0 | 0 | good |
| Sat. 1EO $NH_4$ sulfate | S | 0 | 0 | S | 0 | 0 | S | 0 | 0 | good |

D = dispersable; S = soluble; I = insoluble; Tr = trace
Control result: Solubility: D; 1 h: 0 mL; 24 h: 0.2

Agricultural Dispersant Screening:

The potential of a composition for use as an agricultural dispersant is evaluated by its performance with five typical pesticide active ingredients: atrazine, chlorothalonil, diuron, imidacloprid and tebuconazole. The performance of each dispersant sample is evaluated in comparison with two standard Stepsperse® dispersants: DF-200 and DF-500 (products of Stepan Company).

A screening sample is prepared as shown below for each active. Wetting agents, clays, and various additives are included or excluded from the screening process as needed. The weight percent of pesticide ("technical material") in the formulation depends on the desired active level of the final product. The active level chosen is similar to other products on the market. If this is a new active ingredient, then the highest active level is used.

Samples are evaluated in waters of varying hardness, in this case 342 ppm and 1000 ppm. The initial evaluations are performed at ambient temperature. Other temperatures can be evaluated as desired. The 342 ppm water is made by dissolving anhydrous calcium chloride (0.304 g) and magnesium chloride hexahydrate (0.139 g) in deionized water and diluting to 1 L. The 1000 ppm water is made similarly using 0.89 g of calcium chloride and 0.40 g of magnesium chloride hexahydrate.

Technical material (60-92.5 wt. %), anionic wetting agent (0.5-1.0 wt. %), silica (0.5-1.0 wt. %), and clay (balance) are blended in a suitable container. The blend is milled to a particle size of at least a d(90) of <20μ using a hammer and air/jet mills as needed. Test dispersant (0.1 g) is added to test water (50 mL) in a beaker and stirred 1-2 min. Milled powder containing the technical material (1.0 g) is added to the dispersant solution and stirred until all powder is wet (2-5 min.). The mixture is transferred to a 100-mL cylinder using additional test water for rinsing the beaker and is then diluted to volume. The cylinder is stoppered and inverted ten times, then allowed to stand. Visual inspection is performed at t=0.5, 1.0, 2.0, and 24 hours, and the amount of sediment observed (in mL) is recorded. Trace of sediment="Tr" (see Table 5).

Results appear in Table 5. As shown in the table, both the unsaturated $C_{11}$ alcohol 1EO ethoxylate sulfate, sodium salt, and its saturated analog perform equal to the controls in this test.

TABLE 6

Comparison of Monounsaturated $C_{11}$ Derivatives v. Saturated Analogs: Estimated Phase Region as a Function of % Actives Level[1]

| | Isotropic Clear | Lamellar | Hexagonal | Cubic | Solid/ isotropic | Solid/ gum/ paste |
|---|---|---|---|---|---|---|
| Unsaturated Na sulfate | 0-68 | | | | | 68-100 |
| Saturated Na sulfate | 0-33 | | 33-43 | | | 43-100 |
| Unsat. 1EO Na sulfate | 0-64 | | | | 64-74 | 74-100 |
| Sat. 1EO Na sulfate | 0-36 | 58-72 | 36-58 | | | 72-100 |
| Unsat, 1EO NH$_4$ sulfate | 0-31 | 58-91 | 31-58 | | | 91-100 |
| Sat. 1EO NH$_4$ sulfate | 0-26 | 67-85 | 26-58 | 58-67 | | 85-100 |
| Unsat, 3EO Na sulfate | 0-70 | | | | 70-80 | 80-100 |
| Sat. 3EO Na sulfate | 0-33 | 58-82 | 33-58 | | | 82-100 |
| Unsat. 7EO ethoxylate | 0-38, 57-98[2] | | 38-57 | | | |
| Sat. 7EO ethoxylate | 0-34, 78-98[2] | 63-78 | 34-63 | | | |

[1]All microscopy examinations are performed at room temperature (20-22° C.). Phase boundaries are estimates.
[2]At ~98-100% actives, a two-phase liquid results.

Surfactant Phase Behavior Study:

Phase behavior is observed using an Olympus BH-2 cross-polarized microscope at 100-400X and room temperature (20° C. to 22° C.). The monounsaturated $C_{11}$ alcohol derivatives (sulfates, ethoxylate sulfates, and alcohol ethoxylates) are compared with their saturated analogs.

Samples are prepared by diluting the most concentrated product gradually with deionized water. When the surfactant concentration approaches a phase transition, the concentration is varied at 2-4% intervals to estimate the phase boundary. The actives level reported in Table 6 for each phase boundary is within ±5% of the true boundary.

Samples are loaded between a microscope slide and cover glass and are allowed to equilibrate before observation. Microscopic texture is analyzed and used to determine the phase. For some samples, an AR 2000 rheometer (TA Instruments) is used to measure viscosity at 25° C. to further verify phase behavior.

At low surfactant concentrations, randomly oriented micelles (spheres or cylinders) generally predominate, resulting in a clear or isotropic liquid. As concentration

TABLE 5

Agricultural Dispersants Testing: Anionic Wetting Agent
Sedimentation results at 1 h; 24 h (mL)

| | test water, ppm | DF-200 | DF-500 | Unsaturated 1EO sodium sulfate | Saturated 1EO sodium sulfate |
|---|---|---|---|---|---|
| Diuron | 342 | 1; 2 | 0.5; 1-1.5 | 0.5; 1 | 0.5; 1 |
| | 1000 | 1; 2-2.5 | 0.5-0.75; 2 | 1, 2 | 1, 2 (flock) |
| Chlorothalonil | 342 | 0.25; 1-1.25 | 0.25; 1-1.25 | Tr.; 1 | 0.5; 1 |
| | 1000 | 0.25-0.5; 1.25-1.5 | 2; 3 | 0.5; 1 | 0.5; 2 |
| Imidacloprid | 342 | Tr; 1-1.5 | 0.5-1; 2 | 3, 4 | 1; 2 |
| | 1000 | Tr; 1-1.5 | 0.5-1; 2-2.5 | 3, 3 | 2.5, 2 (flock) |
| Tebuconazole | 342 | Tr; 1.25 | Tr; 1.5 | Tr.; 2 | Tr.; 0.5 |
| | 1000 | Tr; 3 | Tr; 3 | flocked | 5, 3 (flock) |
| Atrazine | 342 | Tr-0.25; 1-1.5 | 0.5; 1 | Tr.; 1 | Tr.; 1 |
| | 1000 | Tr-0.25; 1-1.5 | 6; 3 | 0.5; 1 | 0.5; 1 |
| Rating | | control | control | equal | equal | increases, cylindrical micelles can arrange themselves into either hexagonal or cubic phases, both of which have very high viscosities (10-50K cP at 25° C. for the hexagonal phase, higher for the cubic phase). Thus, in the hexagonal and cubic phases, the surfactant is difficult to process or formulate. Increasing the surfactant concentration more can generate a lamellar phase, where micellar bilayers are separated by water. Because the lamellar phase is pumpable (1-15K cP at 25° C.), compositions having high levels of surfactant actives can be produced. Further concentration of the surfactant can lead to reverse micelles, in some cases generating an isotropic mixture. In sum, phase behavior is important for manufacture, processing, transportation, and formulation of compositions containing surfactants.

An ideal sample is isotropic and clear throughout the entire range of active levels with low viscosity, as this is most likely to avoid any processing issues related with gelling or precipitation during formulation. A lamellar phase is also considered favorable for processing and transportation. Less favorable gel phases include cubic, hexagonal, and solid/gum/paste. All of the samples tested had at least some gel/solid component. The presence of these phases at a particular actives level suggests that processing at or near that actives level will be very difficult.

As shown in Table 6, several of the unsaturated $C_{11}$ derivatives, notably the alcohol sulfate sodium salts and alcohol ether sulfate sodium salts, have isotropic clear phases at actives levels from 0 to 60 or 70 wt. %. This suggests that these surfactants will have wide latitude for formulating at relatively high actives levels. When compared with their saturated analogs, the unsaturated $C_{11}$ derivatives unexpectedly demonstrate favorable phase behavior (combination of isotropic clear and lamellar phases) over a much wider range of actives levels. The results indicate that the unsaturated derivatives will be easier to process than the saturated analogs in intermediate products or fully formulated end-use applications.

Synergy Study: Combining Derivatives with Cationic Surfactant

The surfactant blends tested are prepared at a 1:1 molar ratio without any pH adjustment. Dilutions are made using deionized water to the desired actives level. Actives amounts are wt. % unless indicated otherwise. Appearances are reported at ambient temperature for samples prepared within the last 24 h.

Interfacial tension (IFT) of all the individual components and their blends is measured at 0.1 wt. % active against light mineral oil at ambient temperature using a Kruss DSA-20 pendent drop tensiometer. The drop is blown out at 600 μL/min., and a video is recorded for 100 s. The video frames taken during the last 15 s are analyzed and used for the IFT calculation.

For blends having an IFT less than 0.5 mN/m, the IFT is determined using a spinning drop tensiometer (University of Texas 500) at 25° C. Oil density=0.877 g/cm$^3$ and surfactant density=0.997 g/cm$^3$ are used for the IFT calculation.

The expected IFT for a blend is calculated based on ideal mixing (non-synergistic) using the active component in each blend. The equation used is given as:

$$\text{Expected IFT} = X \ast \text{IFT}a + (1-X) \ast \text{IFT}b$$

where X is the actives % of component A, IFTa is the IFT of component A, and IFTb is the IFT of component B. If the measured IFT for a blend is less than the expected IFT, then the blend is synergistic. If the measured IFT for a blend is higher than the expected IFT, the system is antagonistic.

As shown in Table 7, the unsaturated $C_{11}$ alcohol sulfate, sodium salt, when combined with Ammonyx® Cetac 30, exhibits very high synergy and improved solubility character compared with the saturated analog. Tables 8-10 confirm that the solubility improvement from the unsaturated derivatives is a general trend. Overall, the unsaturated derivatives display a high level of synergy, i.e., as much or more than the saturated analogs.

TABLE 7

Blends of Unsaturated or Saturated $C_{11}$ Na Sulfate with Cationic Surfactants

| Sample Type | anionic | anionic | cationic |
|---|---|---|---|
| Name | Unsat $C_{11}$ Na sulfate | Sat $C_{11}$ Na sulfate | Ammonyx ® Cetac 30 (cetrimonium Cl) |
| anionic:cationic (molar) | 1:1 | 1:1 | |
| Appearance, 1.0% | homogeneous, hazy liquid | separated | clear liquid |
| Appearance, 0.1% | slightly hazy liquid | separated | clear liquid |
| IFT at 0.1% actives (single component) | 5.95 | 16.34 | 0.35 |
| IFT at 0.1% actives/mineral oil (blend) | 0.17 | 2.67 | |
| Calculated IFT (no synergy) | 3.16 | 8.35 | |
| Synergy? | very high | above average | |
| Solubility | good | poor | |

TABLE 8

Blends of Unsaturated or Saturated $C_{11}$ 1EO Na Sulfate with Cationic Surfactants

| Sample Type | anionic | anionic | cationic |
|---|---|---|---|
| Name | Unsat. $C_{11}$ 1EO Na sulfate | Sat. $C_{11}$ 1EO Na sulfate | Ammonyx ® Cetac 30 (cetrimonium Cl) |
| anionic:cationic (molar) | 1:1 | 1:1 | |
| Appearance, 1.0% | separated | separated | clear liquid |
| Appearance, 0.1% | slightly hazy liquid | hazy liquid | clear liquid |
| IFT at 0.1% actives (single component) | 6.18 | 12.52 | 0.35 |
| IFT at 0.1% actives/mineral oil (blend) | 0.13 | 0.23 | |

TABLE 8-continued

Blends of Unsaturated or Saturated C$_{11}$ 1EO Na Sulfate with Cationic Surfactants

| Sample Type | anionic | anionic | cationic |
|---|---|---|---|
| Calculated IFT (no synergy) | 3.27 | 6.44 | |
| Synergy? | very high | very high | |
| Solubility | good | fair-poor | |

TABLE 9

Blends of Unsaturated or Saturated C$_{11}$ 1EO NH$_4$ Sulfate with Cationic Surfactants

| Sample Type | anionic | anionic | cationic |
|---|---|---|---|
| Name | Unsat. C$_{11}$ 1EO NH$_4$ sulfate | Sat. C$_{11}$ 1EO NH$_4$ sulfate | Ammonyx® Cetac 30 (cetrimonium Cl) |
| anionic:cationic (molar) | 1:1 | 1:1 | |
| Appearance, 1.0% | homogeneous hazy liquid | separated | clear liquid |
| Appearance, 0.1% | slightly hazy liquid | hazy liquid | clear liquid |
| IFT at 0.1% actives (single component) | 17.22 | 12.40 | 0.38 |
| IFT at 0.1% actives/mineral oil (blend) | 0.60 | 0.85 | |
| Calculated IFT (no synergy) | 8.8 | 6.2 | |
| Synergy? | very high | high | |
| Solubility | good | fair-poor | |

TABLE 10

Blends of Unsaturated or Saturated C$_{11}$ 3EO Na Sulfate with Cationic Surfactants

| Sample Type | anionic | anionic | cationic |
|---|---|---|---|
| Name | Unsat. C$_{11}$ 3EO Na sulfate | Sat. C$_{11}$ 3EO Na sulfate | Ammonyx® Cetac 30 (cetrimonium Cl) |
| anionic:cationic (molar) | 1:1 | 1:1 | |
| Appearance, 1.0% | hazy liquid | separated | clear liquid |
| Appearance, 0.1% | slightly hazy liquid | hazy liquid | clear liquid |
| IFT at 0.1% actives (single component) | 5.10 | 8.80 | 0.35 |
| IFT at 0.1% actives/mineral oil (blend) | 0.17 | 0.03 | |

TABLE 10-continued

Blends of Unsaturated or Saturated C$_{11}$ 3EO Na Sulfate with Cationic Surfactants

| Sample Type | anionic | anionic | cationic |
|---|---|---|---|
| Calculated IFT (no synergy) | 2.73 | 4.58 | |
| Synergy? | high | very high | |
| Solubility | good | fair-poor | |

The preceding examples are meant only as illustrations; the following claims define the invention.

We claim:

1. A process which comprises reacting a composition comprising a monounsaturated C$_{10}$-C$_{12}$ alcohol with an alkoxylating agent, a sulfating agent, or an alkoxylating agent followed by a sulfating agent to make, respectively, an alkoxylate, a sulfate, or an ether sulfate.

2. The process of claim 1 wherein the monounsaturated C$_{10}$-C$_{12}$ alcohol or alkoxylate is reacted with sulfur trioxide in a falling-film reactor, followed by neutralization.

3. A process for making an internally monounsaturated C$_{10}$-C$_{12}$ alcohol sulfate or ether sulfate, the process comprising reacting a terminally monounsaturated C$_{10}$-C$_{12}$ alcohol or alkoxylate with sulfur trioxide in a falling-film reactor, followed by neutralization.

4. A composition comprising water and 1 to 99 wt. % of a surfactant, wherein the surfactant comprises an ether sulfate of the formula:

$$CH_2\!\!=\!\!CH\!\!-\!\!(CH_2)_9\!\!-\!\!O\!\!-\!\!(EO)_n\!\!-\!\!SO_4^-M^=$$

wherein n is the average number of EO units and has a value from 1 to 5, and M is Na, K, Li, or NH$_4$.

5. The composition of claim 4 wherein M is Na or NH$_4$.

6. The composition of claim 4 wherein M is Na and n is 1 or 3.

7. The composition of claim 4 wherein M is NH$_4$ and n is 1.

8. A composition comprising water and 1 to 99 wt. % of a surfactant comprising sulfates of undecylenic alcohol, wherein the surfactant comprises:
 (a) 40 to 60 wt. % of a monounsaturated C$_{11}$ primary alcohol sulfate; and
 (b) 40 to 60 wt. % of a secondary hydroxyalkyl C$_{11}$ primary alcohol sulfate.

9. The composition of claim 8 comprising 2 to 98 wt. % of the surfactant.

10. The composition of claim 8 wherein the surfactant further comprises 0.1 to 20 wt. % of sulfonated products.

11. The composition of claim 8 made by sulfating undecylenic alcohol with sulfur trioxide in a falling-film reactor, followed by neutralization.

* * * * *